United States Patent [19]

Lorch

[11] Patent Number: 4,776,358

[45] Date of Patent: Oct. 11, 1988

[54] FLOSS EMPLOYING MICROPOROUS TAPES SANDWICHING PASTE DENTIFRICE

[76] Inventor: Leonard Lorch, P.O. Box 4343, Stanford, Calif. 94309

[21] Appl. No.: 175,665

[22] Filed: Mar. 17, 1988

Related U.S. Application Data

[63] Continuation-in-part of Ser. No. 910,733, Sep. 23, 1986, abandoned.

[51] Int. Cl.$^4$ .............................................. A61C 15/00
[52] U.S. Cl. ..................................... 132/321; 433/216
[58] Field of Search .............. 132/89, 91, 92 R, 92 A, 132/93; 433/142, 166

[56] References Cited

U.S. PATENT DOCUMENTS

| | | | |
|---|---|---|---|
| 1,069,874 | 8/1913 | Hanscom | 132/93 |
| 1,138,479 | 5/1915 | Hough | 433/142 |
| 1,833,842 | 11/1931 | Leonard | 433/142 |
| 2,223,952 | 12/1940 | Darmody | 132/84 D |
| 2,667,443 | 1/1954 | Ashton | 132/91 |
| 3,187,390 | 6/1967 | Gore | 174/102 R |
| 3,330,732 | 7/1967 | Muhler | 167/93 |
| 3,491,776 | 1/1970 | Fleming | 132/89 |
| 3,699,979 | 10/1972 | Muhler et al. | 132/89 |
| 3,863,655 | 2/1975 | Smith | 132/91 |
| 3,942,539 | 3/1976 | Corliss | 132/79 E |
| 3,943,949 | 3/1976 | Ashton et al. | 132/89 |
| 3,957,067 | 6/1976 | Ferraro et al. | 132/89 |
| 4,033,365 | 7/1977 | Klepak et al. | 132/89 |
| 4,105,120 | 8/1978 | Bradberry | 132/92 R |
| 4,237,911 | 12/1980 | White | 132/89 |
| 4,256,806 | 3/1981 | Faydit | 428/378 |
| 4,304,245 | 12/1981 | Lichfield | 132/89 |
| 4,435,380 | 3/1984 | Pader | 424/49 |
| 4,450,849 | 5/1984 | Cerceo et al. | 132/89 |
| 4,548,219 | 10/1985 | Newman et al. | 132/91 |
| 4,570,653 | 2/1986 | Wolf | 132/91 |
| 4,583,564 | 4/1986 | Finkelstein et al. | 132/91 |

FOREIGN PATENT DOCUMENTS

2128133 4/1984 United Kingdom .

OTHER PUBLICATIONS

Lorch, Medical Protex '84, pp. 333–334, JADA, Apr. 1985, pp. 545–547.
The Wall Street Journal, Jun. 20, 1986, p. 19, Jerry E. Bishop, "Tiny Sponges Try to Capture a Big Role in Many Products".

Primary Examiner—Gene Mancene
Assistant Examiner—Adriene J. Lepiane

[57] ABSTRACT

An improved dental flossing material and method of making the same is disclosed. The flossing material in the form of a tape is formed of expanded polytetrafluoroethylene (PTFE) folded longitudinally to form a pair of laminae defining a recess therebetween in which an abrasive or non-abrasive cleaning material is disposed. During the cleaning procedure, material flows from the free edges of the tape to become deposited upon the surfaces of the teeth and adjacent gingiva. Due to changes in light transmitting quality of the tape, a visual and reversible indication of prior use becomes apparent. In the manufacture of the tape, the PTFE, which is microporous, is coated on one surface thereof with a moist dentifrice which may be suitably thinned using a volatile vehicle. After folding, the moisture evaporates through the microporous structure to partially dry the dentifrice to a point where the abrasive particles attain a useful degree of shear, following which the finished article is enclosed in an airtight or hermetically sealed envelope to maintain a useful moisture level. Optionally, for greater longevity the dentifrice may contain a humectant.

17 Claims, 1 Drawing Sheet

U.S. Patent   Oct. 11, 1988   4,776,358
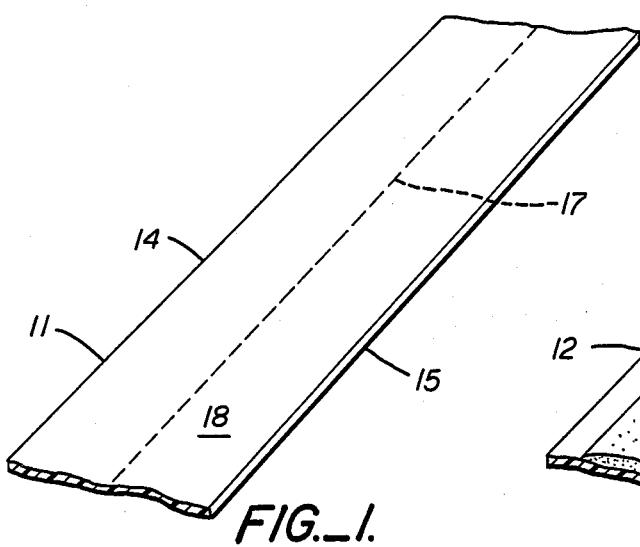
FIG._1.
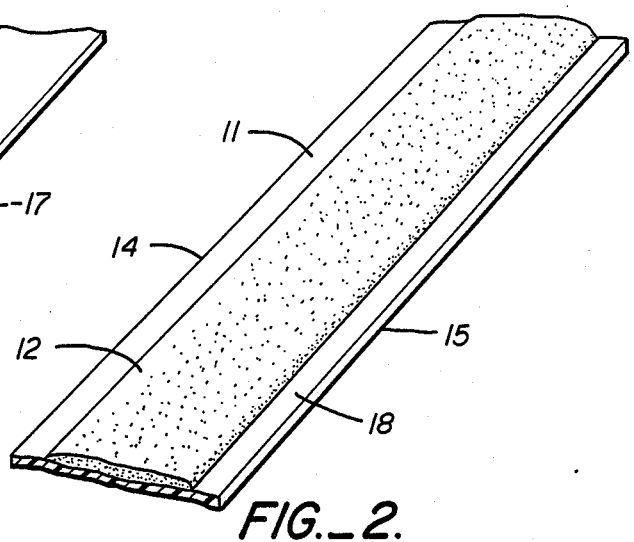
FIG._2.
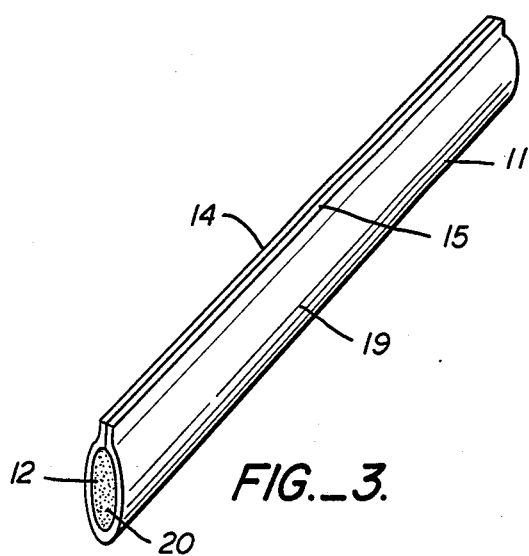
FIG._3.
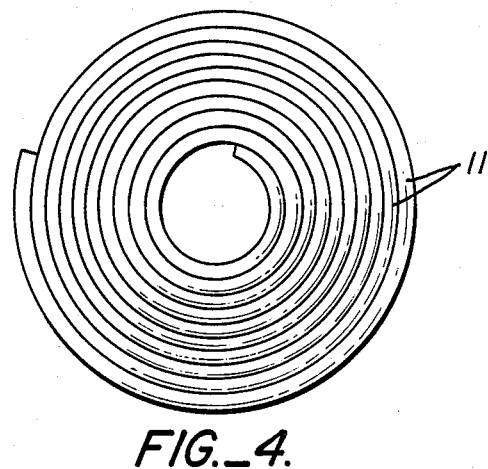
FIG._4.
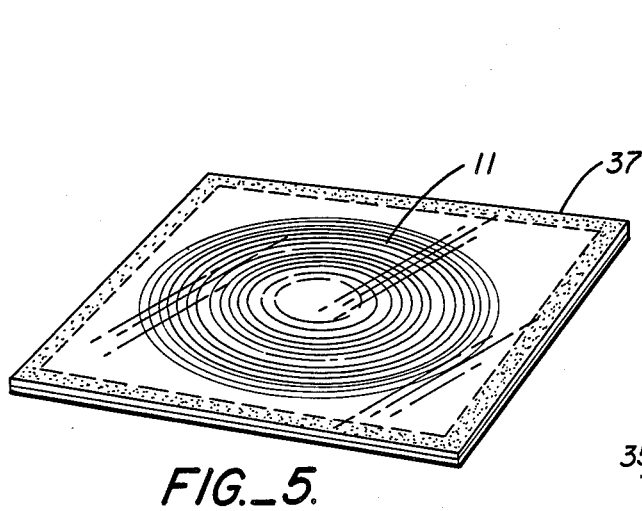
FIG._5.
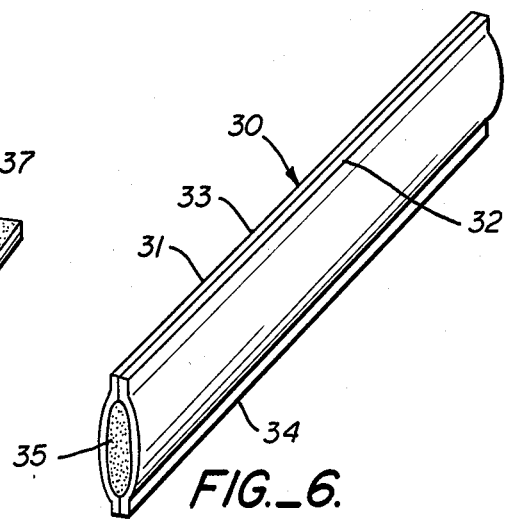
FIG._6.

FLOSS EMPLOYING MICROPOROUS TAPES SANDWICHING PASTE DENTIFRICE

BACKGROUND—CROSS REFERENCE TO RELATED APPLICATION

This application is a continuation-in-part of Ser. No. 910,733, filed 1986-9-23, now abandoned.

BACKGROUND: FIELD OF INVENTION

This invention relates generally to the field of dental cleaning materials, and particularly to an improved dental flossing tape which may be used conveniently by those possessing only ordinary skill, and which offers advantages not heretofore available to the general public.

BACKGROUND: DESCRIPTION OF PRIOR ART

Typically, the use of prior art technology employs a waxed or non-waxed thread of textile material which is passed between the teeth and moved in the interstice to dislodge entrapped food particles, and to debride dental plaque and other debris. This operation will normally result in contacting adjacent gingiva as well. The thread or flat tape will remove unwanted material, but is not capable of providing a polishing effect on the teeth.

For the professional, there are available various forms of monoplanar tapes which can be manually coated with a polishing material and applied to complete professional cleaning procedures. This operation is somewhat messy, necessitating the soiling of the fingers, and, as a result, there is little possibility of acceptance of the same by the lay public.

Conventional brushing with a toothbrush, particularly when carefully performed, does much to maintain the teeth in cleaned condition. However, brushing does not reach the spaces between the teeth to any substantial depth, particularly in those areas between the teeth and below the gums. Therefore such brushing must be supplemented by effective flossing which will bring cleaning material to the otherwise unreached areas.

OBJECTS AND ADVANTAGES

Accordingly several objects and advantages of the invention are to provide an improved flossing means, to provide a flossing means which polishes the teeth, and to provide a flossing tape which is neat to use, is economical, easy to fabricate, etc. Further objects and advantages will become apparent from a consideration of the ensuing description and accompanying drawings.

SUMMARY OF THE INVENTION

Briefly stated, the invention contemplates the provision of an improved flossing tape capable of carrying a suitable dentifrice, including abrasive material. Use of the same will not result in soiling the fingers of the user, but will allow ready flow of the dentifrice to the outer surfaces of the tape during use. Thereby a cleaning procedure is obtained which approaches in efficacy that obtained by professional personnel.

To this end, the disclosed embodiments comprise a microporous tape of synthetic resinous material, typically polytetrafluoroethylene, in which the dentifrice is positioned, during manufacture between a pair of lamina in relatively dehydrated condition, to be activated by contact of the outer surfaces of the lamina with saliva and/or other liquids present in the oral cavity. It is to be understood that the use of the term "microporous" herein encompasses micropores or microvoids. Some of the dentifrice flows through the pores of the laminae, and the remainder thereof exudes from the free longitudinal edges of the tape.

While a number of synthetic resinous materials are useful for the contemplated purpose, I have found most suitable, expanded and microporous polytetrafluoroethylene (PTFE) to be ideal. This material is presently commercially available in a flat and microporous filament known as weaving fiber in sizes ranging from about 100 to 200 denier to greater than 2,400 denier (a filament of one denier weighs 50 mg per 450 m of length). Such a fiber has a minimum breaking tenacity of three grams per denier, and typical thickness of 25.4 microns (1 mil).

As a dentifrice, many commercially available toothpastes and gels are suitable. The dentifrice can be coated upon the laminae as is, or it can first be thinned with a volatile vehicle such as ethanol. After application, the dentifrice is enclosed between the laminae, and some of the moisture content is allowed to evaporate through the pores of the microporous laminae to a degree where abrasive particles offer a suitable shear for cleaning or polishing purposes. The tape is then suitably packaged in an airtight or hermetically sealed enclosure so as to maintain the desired moisture level prior to use. When put into use, owing to the force exerted on the exposed surfaces of the tape, the dentifrice is caused to exude from the tape, wherein it may mix with saliva, water, or other fluid present in the oral cavity which will assist in spreading the same over the surfaces of the teeth as the tape is moved between the individual teeth.

Optionally the dentifrice may also ciontain a humectant, such as disclosed in Pader U.S. Pat. No. 3,538,230 (1970), in order that the floss will remain stable and moist for a longer period of time.

BRIEF DESCRIPTION OF THE DRAWINGS

In the drawings, to which reference will be made in the specification, similar reference characters have been engaged to designate corresponding parts throughout the several views.

FIG. 1 is a fragmentary view in perspective showing a first step in the manufacture of an embodiment of the invention.

FIG. 2 is a view in perspective showing a second step in the method.

FIG. 3 is a view in perspective showing a third step in the method.

FIG. 4 is a view in elevation showing a completed tape in coiled condition ready for packaging.

FIG. 5 is a view in elevation, partly broken away to show detail of a completed article in packaged condition.

FIG. 6 is a view in perspective of a second embodiment of the invention.

FIRST EMBODIMENT—FOLDED TAPE—FIGS. 1 TO 3

In accordance with the first embodiment of the invention, the device is described by its method of fabrication as illustrated in the sequential steps of FIGS. 1 to 5. The starting material is a microporous base element (FIG. 1) which is coated by a dentifrice 12 (FIGS. 2 and 3).

Element 11 is formed by parallel strips (FIG. 1) of indefinite length having first and second longitudinal edges 14 and 15, a medially disposed axial fold line 17, and inner and outer surfaces 18 and 19 defining a planar interstice 20 therebetween.

Dentifrice 12 may consist of a variety of ingredients. I have found that many commercially available toothpastes and gels are suitable. The former are water based suspensions including particulate abrasives which, depending upon brand and composition, may vary from about one micron to about twenty microns average particle size. Optionally, for greater longevity the dentifrice may contain a humectant. Ideally, the particle size is sufficiently small as to be capable of limited passage through the pores of the microporous strips, although this characteristic is not essential.

Dentifrice 12 is applied to inner surface 18 of element 11 by any suitable coating method. This can be assisted by the thinning of the dentifrice with the addition of a volatile vehicle, such as ethanol, which evaporates through the pores of the microporous material without difficulty. If necessary, this process can be expedited by the addition of heat in a well known manner.

SECOND EMBODIMENT—FIG. 6

A second embodiment 30 (FIG. 6) differs from the first embodiment in that separate strips are provided instead of a single strip which is longitudinally folded. Thus, a pair of strips or laminae 31 and 32 are each bounded by first and second longitudinal edges 33 and 34. A coating 35 may be applied to one or both inner surfaces prior to assembly.

COILING AND PACKAGING—FIGS. 4 and 5

In either the first or the second embodiment, the article is suitably packaged by coiling the same (FIG. 4) prior to insertion into an airtight or a hermetically sealed package 37 (FIG. 5), so that desired moisture content may be maintained until the time of use.

With the opening of the package and the uncoiling of the article, the product is used as with any dental tape by tensing the same between the fingers of the user and inserting the same between the teeth, followed by further movements altogether called a flossing procedure. As the tape is moved, a pressure exerted on the sides of the same will cause the dentifrice to exude from the free longitudinal edges in the areas between the teeth and below the gums, so that the outer surfaces of the article will engage the same and perform a cleaning or polishing action. In the case where the strips are of PTFE, contact with the teeth under pressure will cause a visible change in the translucency of the product, so that the fact that the product has been previously used is readily apparent. As the dentifrice exudes, it mixes with fluids present in the oral cavity, which causes a resuspension of any agglomerated particles, and facilitates flow of the dentifrices over the teeth during the cleaning or polishing operation.

The following examples are to be considered as illustrative, and not exhaustive of available modifications in the spirit of the invention. In the case of each laminate, the microporous material has a minimum tensile strength of three grams per denier and consists of expanded PTFE fiber obtainable commercially under the trademark GORE-TEX, and manufactured by W. L. Gore & Associates, Inc. of Newark, Del. The dentifrices employed are commercially available as consumer products, suitably modified for use in conjunction with a dental tape.

EXAMPLE I

| | |
|---|---|
| Fiber size: | 2,400 denier |
| Thickness of base: | 25.4 microns (1 mil) |
| Width of tape: | 7/32 to ¼ inch |
| Tensile strength: | About 7.3 Kg (16 pounds) |
| Applied dentifrice: | Colgate toothpaste from tubes (Colgate-Palmolive) |

Procedure:

The tape is cut to a convenient length of 46 cm (18 inches) and doctor blade coated with the dentifrice to a thickness averaging in the range of about 0.25 mm (10 mils) to about 0.76 mm (30 mils). The tape was next folded longitudinally upon itself and lightly pressed together, leaving the longitudinal edges thereof in substantially abutted condition. In elongated condition, the tapes were permitted to partially dry at room temperature for approximately eighteen hours, following which each length of tape was coiled and placed in an air-tight container, namely a synthetic resinous envelope, such as those sold under the trademark ZIP-LOCK of Dow Chemical Co. In this condition, the tapes were stored over a period of several months prior to use. Upon opening the same, the tapes were found to be supple, the dentifrice being adequately stabilized without oozing from the abutted edges of the tape prior to actual use. Using the tapes in normal manner, loss in taste was detected, but when the tapes were stored for a week, then no substantial loss in taste was detected. As the tapes were passed between the teeth, additional moisture present within the oral cavity activated the dentifrice sufficient to cause it to flow from the abutted longitudinal edges. It was found that the tape changed translucency in those areas where pressure exerted upon the sides of the tape, as during a flossing operation, caused temporary changes in translucency, which were restored after use when the tape dried, or was partially dried and tensed in a longitudinal or transverse direction. When tensed and moved to floss between all contacting teeth of the dentition the tape did not break, and demonstrated little or no fraying of the PTFE.

In another version of this example, when the 6.4 mm (0.25 inch) wide base material was macroscopically punched with 1.6 mm (0.625 inch) holes spaced apart longitudinally about every 1.3 cm (0.5 inch), and then coated and partially dried in a similar manner, and then used in a similar flossing procedure, the tape demonstrated increased fraying.

EXAMPLES 2-7

Using the unpunched base material of the above described procedure so as to lamnate together two separate strips of 400 denier each with about 25.4 microns (1 mil) thickness for each strip and about 1.1 Ka minimum breaking tenacity of each strip, various dentifrices were substituted with equally favorable result. Suitable materials include Crest tartar control formula toothpaste from a tube (Procter & Gamble), Pepsodent toothpaste from a tube (Lever Brothers), Ultrabrite toothpaste from a tube (Colgate), Zact (Lion Corp., made in Japan), and Check-Up (Henkel, made in West Germany), and Close-Up gel (Lever Brothers). Because of the consistency of certain of the gels, there was a slight tendency to separate within the tape interstice upon partial stabilization, which separation does not appear to affect the efficacy of the device when used. During the procedure of flossing the dentition, each strip of 400 denier in the laminate did not normally break in the mouth. There was little or no fraying of PTFE.

Where desired, for a given thickness such as 25 microns (1 mil), the fiber size of each strip may be varied, ranging from a low of approximately 300 to 400 denier, up to 2,400 denier. Below the lower level there are problems of suitably abutting strips of the laminate. Below the thickness of 25.4 microns (1 mil), for example at about 19.05 microns (0.75 mil), there is a slight advantage that corresponds to about 300 to 1,800 denier. Above the upper levels no advantage in flossing effect appears to be obtainable.

Partial stabilization can be obtained during a shorter period of time by applying heat to the product to drive off excess moisture through the microvoids of the tape. Where, owing to the thickness of the dentifrice, difficulty is encountered in spreading the same, spreadability may be improved by the addition of small amounts of a volatile vehicle, such as ethanol, which evaporates through the microvoids of the tape during the stabilizing procedure. Most dentifrices contain abrasive particles ranging from 1 to 20 microns, with a suitable average being around 3 to 5 microns. Adequate flow of the dentifrice occurs from the abutted longitudinal edges during use.

The obtaining of a proper degree of stabilization depends, to some extent, on the manner in which the product is packaged for commercial use. While most conveniently, the product is stabilized (through evaporation of moisture) to a degree where the abutted edges will not shift when sheared between the thumb and finger of the user, in some cases, it may be desirable to package the product in a more moist state, in the interest of preserving volatile flavoring oils, so that when the airtight container is opened, further partial stabilization may occur prior to use, particularly when several lengths of product are packaged within a single container.

EXAMPLE 8

Using examples 1-7, an airtight container was substituted by a sealed hermetic enclosure with no substantial loss in taste detected after storage for several months.

EXAMPLE 9

Using examples 1-7, but before the commercially available dentifrices listed are respectively applied to the laminae, said dentifrices are mixed with flexible microsponges that contain the flavor oil(s) particular to that dentifrice. Such microsponges with filling with a flavor oil are commercially obtainable from Advanced Polymer Systems, Inc., (API) of Redwood City, Calif., subject to FDA approval.

Then following the procedures in examples 1-7, the tapes were stored over a period of several months prior to use. Upon opening, no substantial loss in taste was detected when the laminae and its dentifrice containing microsponges were moved between and pressed against teeth in a flossing procedure that released flavor oil from the microsponges of the exuded dentifrice.

I wish it to be understood that I do not consider the invention to be limited to the precise details of structure shown and set forth in this specification, for obvious modifications will occur to those skilled in the art to which the invention pertains. Accordingly the scope of the invention should be determined, not by the examples given, but only by the appended claims and their legal equivalents.

I claim:

1. An improved article for flossing the teeth, comprising:
    a base element including first and second laminae of thin, flexible microporous polytetrafluoroethylene having a pair of inwardly facing, opposed surfaces defining an interstice; said laminae being thin and strong enough to floss between contacting teeth;
    a water-suspendable dentifrice containing a particulate abrasive material applied to said opposed surfaces as a moist coating which is partially dried by evaporation through said microporous laminae such that a quantity of the water-suspendable dentifrice remains sandwiched between said laminae;
    whereby said dentifrice may be resuspended by saliva and other liquids in the oral cavity when said article is applied to the teeth by being released at the free edges of said laminae under compression thereon to contact tooth surfaces during a flossing procedure.

2. An article as set forth in claim 1 in which said dentifrice is in paste form.

3. An article as set forth in claim 1 in which said dentifrice is in gel form.

4. An article as set forth in claim 1, further comprising an airtight enclosure surrounding said articles to maintain a useful moisture content in said article prior to use.

5. An article as set forth in claim 1, further comprising a hermetically sealed enclosure surrounding said article to maintain a useful moisture content in said article prior to use.

6. An article as set forth in claim 1 wherein said dentifrice contains microsponges containing flavor oil.

7. An article as set forth in claim 1 wherein said dentifrice contains a humectant.

8. A process for manufacturing a dental floss product comprising the step
    (a) providing planar strips of thin flexible microporous material;
    (b) providing a dentifrice in fluid form having a substantial moisture content and having suspended abrasive particles;
    (c) coating said strips on a single surface thereof with said dentifrice;
    (d) abutting pairs of coated surfaces under pressure to substantially enclose said dentifrice therebetween; and
    (e) partially drying said dentifrice by evaporation of the moisture content thereof through the microvoids of said microporous material to a level wherein said abrasive particles have a useful degree of shear.

9. In the process set forth in claim 8, the additional step of placing the abutted strips in a hermetically sealed enclosure to maintain the moisture content of the dentifrice at a useful value prior to use.

10. In the process set forth in claim 8, the additional step of thinning the dentifrice with a volatile vehicle prior to it application to the coated surfaces of the lamina.

11. The process set forth in claim 10 in which said vehicle is ethanol.

12. In the proess set forth in claim 8, the additional step of placing the abutted strips into an airtight enclosure to maintain the moisture content of the dentifrice at a useful value prior to use.

13. The process set forth in claim 8 in which said dentifrice contains a humectant.

14. A dental floss for flossing teeth, comprising:
two elongated strips of a flexible microporous polytetrafluoroethylene material, each strip having a substantially continuous surface which faces and is coextensive with the corresponding surface of the other of said strips, said strips being thin and strong enough to floss between contacting teeth, and
a layer of a water-suspendable dentifrice containing moisture and a particulate abrasive material, said layer being positioned between and applied to both of said surfaces of said strips, such that said strips sandwich said dentifrice to form a continuous laminar assembly, and so that moisture in said dentifrice can escape through the micropores of said strips.

15. The dental floss of claim 14 wherein said two strips are integral and are joined by an elongated fold.

16. The dental floss of claim 14 wherein said two strips are separate.

17. The dental floss of claim 14 wherein said dentifrice also contains a humectant.

* * * * *

UNITED STATES PATENT AND TRADEMARK OFFICE
CERTIFICATE OF CORRECTION

PATENT NO. : 4,776,358
DATED : 1988 Oct 11
INVENTOR(S) : Lorch, Leonard

It is certified that error appears in the above-identified patent and that said Letters Patent are hereby corrected as shown below: Title page:

Abstract page, under "U.S. PATENT DOCUMENTS", line 17, change "Faydit" to --Snyder--.

Column 2, line 33, change "ciontain" to --contain--.

Column 4, line 46, change "(0.625 inch)" to --(.0625 inch)--.

Column 4, line 56, change "1.1 Ka" to --1.1 Kg--.

Claim 1, line 12, change "the" to --said--.

Claim 4, line 2, change "articles" to --article--.

Claim 8, line 2, change "step" to --steps of:--.

UNITED STATES PATENT AND TRADEMARK OFFICE
CERTIFICATE OF CORRECTION

PATENT NO. : 4,776,358
DATED : October 11, 1988
INVENTOR(S) : Lorch, Leonard

It is certified that error appears in the above-identified patent and that said Letters Patent is hereby corrected as shown below:

Claim 10, line 3, change "it" to --its--.

Signed and Sealed this

Twenty-eighth Day of February, 1989

*Attest:*

DONALD J. QUIGG

*Attesting Officer*  *Commissioner of Patents and Trademarks*